US00PP32944P3

(12) United States Plant Patent
Beckman

(10) Patent No.: US PP32,944 P3
(45) Date of Patent: Mar. 30, 2021

(54) CALLA LILY PLANT NAMED 'NIGHT CLUB'

(50) Latin Name: *Zantedeschia sprengeri*
Varietal Denomination: Night Club

(71) Applicant: Dümmen Group B.V., De Lier (NL)

(72) Inventor: Peter Beckman, Santa Cruz, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,421

(22) Filed: Oct. 1, 2019

(65) Prior Publication Data

US 2020/0113105 P1 Apr. 9, 2020

Related U.S. Application Data

(60) Provisional application No. 62/766,205, filed on Oct. 4, 2018.

(51) Int. Cl.
*A01H 6/10* (2018.01)
*A01H 5/02* (2018.01)
*A01H 6/56* (2018.01)

(52) U.S. Cl.
USPC ..... Plt./490
CPC ..... *A01H 6/56* (2018.05)

(58) Field of Classification Search
USPC ..... Plt./490
CPC ..... A01H 6/10; A01H 5/02
See application file for complete search history.

*Primary Examiner* — Keith O. Robinson
(74) *Attorney, Agent, or Firm* — The Webb Law Firm

(57) ABSTRACT

'Night Club' is a new variety of calla lily plant having purple colored spathes that have a funnel shape. The flower stems are strong and long lasting. The leaves are green with no maculations present.

1 Drawing Sheet

Botanical classification: *Zantedeschia sprengeri*.
Varietal denomination: 'Night Club'.

BACKGROUND OF THE NEW PLANT

The present invention comprises a new and distinct cultivar of calla lily, botanically known as *Zantedeschia sprengeri* and hereinafter referred to by the cultivar name 'Night Club'.

'Night Club' is a product of a planned breeding program having the objective of creating *Zantedeschia* varieties for pot flower production in a wide range of colors and classic flower shapes. 'Night Club' was selected in 2005 in Moss Landing, Calif. as an inbred seedling selected from an open-pollinated population and self-pollinated for many generations. As such, its exact parentage is unknown and comparisons thereto cannot be provided.

The new variety was first asexually reproduced through tissue culture shoot propagation in October of 2006 in Moss Landing, Calif. Asexual reproductions of 'Night Club' have demonstrated that the combination of characteristics as herein disclosed for the new variety are retained and reproduced true to type through successive generations of asexual reproduction.

The following observations, measurements and comparisons describe plants grown in 15 cm pots at 77 days from planting in 't Zand, The Netherlands under greenhouse conditions, which approximate those generally used in horticultural practice. Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Night Club' which, in combination, distinguish this calla lily as a new and distinct cultivar:

1. Purple colored spathes;
2. Funnel shaped spathes; and
3. Firm, long-lasting peduncles.

Table 1 provides a comparison of 'Night Club' to similar *Zantedeschia sprengeri* varieties 'Night Life' (unpatented) and 'Paco' (U.S. Plant Pat. No. 24,246).

TABLE 1

| Comparison variety | Differing trait(s) | Comparison expression | Present variety expression |
|---|---|---|---|
| 'Night Life' | Spathe color | Red-Purple Group RHS 59A | Purple Group RHS N79A to N79B |
| | Throat spot | Present | Absent |
| 'Paco' | Flowering time | 70-75 days to flower | 40-45 days to flower |

Further, 'Night Club' has more trumpet shaped, smoother edged, and narrower inflorescences than 'Night Life'. 'Night Club' flowers 7 days earlier than 'Night Life'. Also, 'Night Club' exhibits superior peduncle strength (21 days to nodding) than 'Night Life' (12 days to nodding).

BRIEF DESCRIPTION OF THE DRAWING

The accompanying photographic drawing illustrates the new variety at 77 days from planting, with the colors being as nearly true as is possible with color illustrations of this type.

DESCRIPTION OF THE NEW PLANT

Type: Deciduous.
*Form.*—Semi-spreading.

*Average spread.*—27-41 cm.
*Branch number.*—Average.
*Branch color.*—Brown Group RHS 200B to 200C.
*Height of leaf canopy above the soil.*—11-19 cm.
*Height of top of inflorescences above the soil.*—20-28 cm.
*Number of inflorescences per tuber.*—16-18 cm in diameter: 7-15.
*Lastingness of inflorescences on the plant.*—About 14 days.
*Main use.*—Potted plant.
*Average time of flowering.*—Tubers planted in the field in May in 't Zand, The Netherlands bloom in July. Tubers planted in a greenhouse in February in 't Zand, The Netherlands bloom in April.
*Disease/pest resistance.*—Strong tolerance to *Pythium* root rot and *Erwinia* bulb soft rot.
*Hardiness.*—Not tested.

Leaves:
*Number per plant.*—17-29.
*Width.*—4-6 cm, with broadest position slightly below the middle.
*Length.*—17-23 cm.
*Shape.*—Lanceolate.
*Apex.*—Apiculate.
*Base.*—Attenuate.
*Margin.*—Entire.
*Color.*—Upper surface: Yellow-Green Group RHS 146B, with no maculations present. Lower surface: Green Group RHS 143C, with no maculations present.
*Surface texture.*—Smooth (both surfaces).
*Leaf venation.*—Pattern: Pinnate. Color: Yellow-Green Group RHS 144C to 144D.
*Lobes.*—None present.
*Petiole.*—Length: 11-20 cm. Diameter: 10-12 mm. Texture: Smooth. Shape: Cylindrical. Strength: Medium to weak. Color: Upper surface: Green Group RHS 143B to 143C. Lower surface: Yellow-Green Group RHS 144B to 144C.

Spathe:
*Length.*—5-8 cm.
*Width.*—3.5-4.5 cm.
*Fragrance.*—None.
*Shape.*—Funnel.
*Texture.*—Smooth.
*Apex.*—Caudate.
*Base.*—Attenuate.
*Margin.*—Entire.
*Color.*—Throat spot: Absent. Upper surface: Purple Group RHS N79A to N79B. Lower surface: Purple Group RHS N79A to N79B.

Spadix:
*Length.*—35-50 mm.
*Diameter.*—8-11 mm.
*Color.*—Yellow-Orange Group RHS 16B to 16C.
*Position relative to spathe.*—Upright from base.
*Apex.*—Rounded and Yellow-Orange Group RHS 23A to 23B.
*Pollen amount.*—Abundant.

Peduncle:
*Strength.*—Strong and erect, with no nodding observed until day 21.
*Length.*—20-29 cm.
*Diameter.*—8-12 mm.
*Texture.*—Smooth.
*Color.*—Base: Yellow-Green Group RHS 144C to 144D. Upper portion: Purple Group RHS N77A.

Seeds:
*Number/flower.*—25.
*Length.*—2.2-4.3 mm.
*Diameter.*—2.1-3.1 mm.
*Color.*—White Group RHS 155B to 155C.

Reproductive organs:
*Anther.*—Shape: Round. Length: Less than 1 mm. Color: Yellow Group RHS 8B to 8C.
*Filament.*—Length: Less than 1 mm. Color: White Group RHS 155D.
*Style.*—Length: Less than 1 mm. Color: Yellow Group RHS 8B to 8C.
*Pistil.*—Number: 15-30. Length: About 1 mm.
*Stigma.*—Shape: Round. Length: Less than 1 mm. Diameter: Less than 1 mm.
*Ovaries.*—Texture: Smooth. Length: Varies between 1 to 10 mm. Diameter: Varies between 1 to 10 mm. Color: Top: Yellow Group RHS 3A. Bottom: Yellow Group RHS 4B to 4C.

I claim:

1. A new and distinct variety of calla lily plant named 'Night Club' as herein described and illustrated.

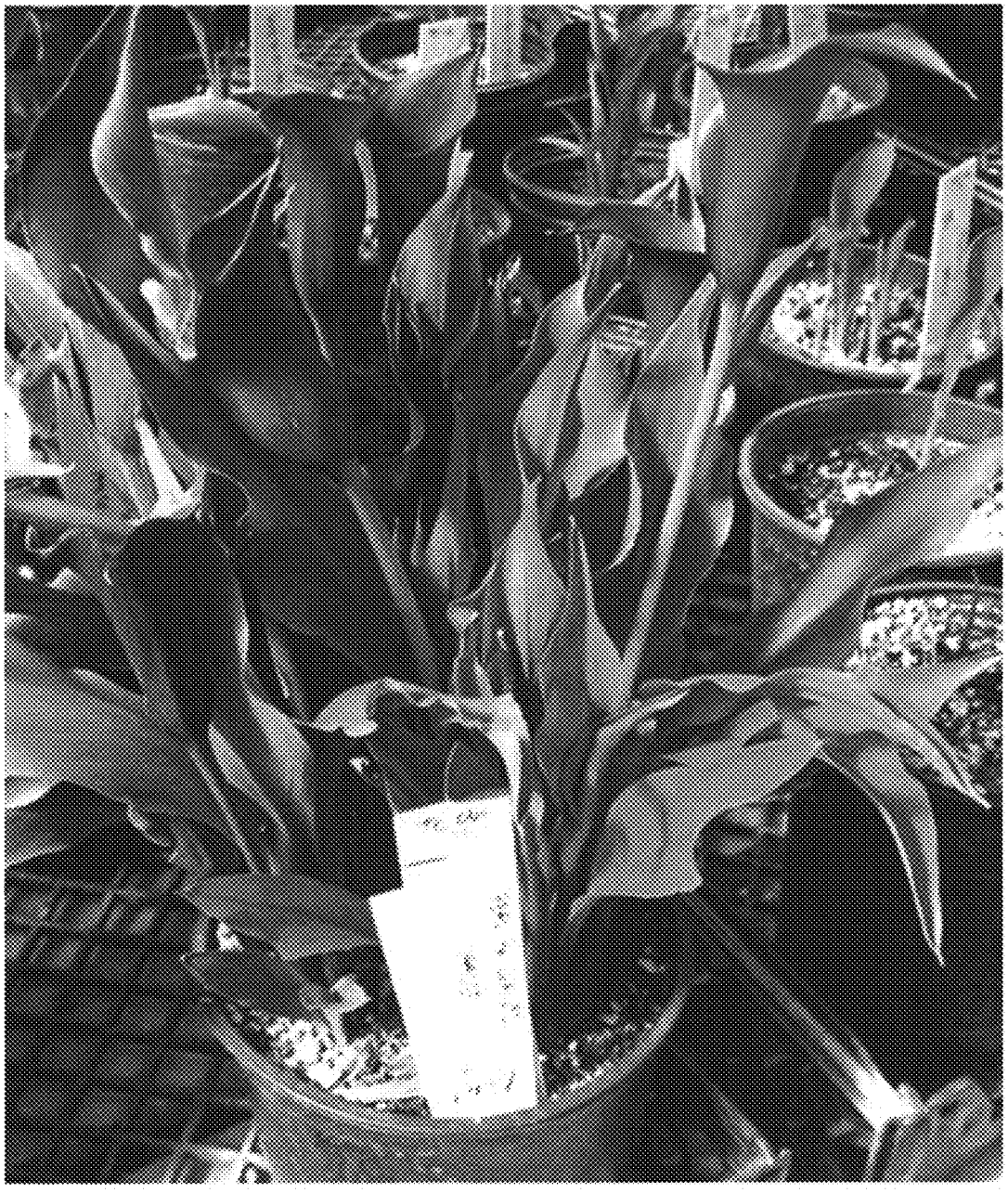

* * * * *